United States Patent

Shaw et al.

[11] Patent Number: 5,952,184
[45] Date of Patent: *Sep. 14, 1999

[54] METHODS FOR DETERMINING PLATELET FUNCTION

[75] Inventors: Andrew R. E. Shaw, Edmonts; Michael W. Stewart, St. Albert, both of Canada

[73] Assignee: Alberta Cancer Board, Edmonton, Canada

[*] Notice: This patent is subject to a terminal disclaimer.

[21] Appl. No.: 08/433,084

[22] Filed: May 3, 1995

Related U.S. Application Data

[63] Continuation of application No. 07/985,679, Dec. 3, 1992, Pat. No. 5,427,913.

[51] Int. Cl.$^6$ ...................... G01N 33/546; G01N 33/547; G01N 33/567; C12Q 1/56
[52] U.S. Cl. ...................... 435/7.21; 435/7.8; 435/13; 436/503; 436/533; 436/534
[58] Field of Search ................... 435/7.21, 7.8, 435/13; 436/503, 533, 534, 69

[56] References Cited

U.S. PATENT DOCUMENTS

| | | | |
|---|---|---|---|
| 5,196,309 | 3/1993 | Ginsberg | 435/7.21 |
| 5,427,913 | 6/1995 | Shaw et al. | 435/7.21 |

OTHER PUBLICATIONS

Schwartz et al., "Insoluble Fibronectin Activates the Na/H Antiporter by Clustering and Immobilizing Integrin $\alpha_5\beta_1$ Independent of Cell Shape", Proc. Natl. Acad. Sci. USA 88:7849–7853 (1991).

Griffith et al., "Platelet Activation by Immobilized Monoclonal Antibody: Evidence for a CD9 Proximal Signal", Blood 78:1753–1759 (1991).

Coller et al., "Interaction of Normal, Thrombasthenic, and Bernard–Soulier Platelets With Immobilized Fibrinogen: Defective Platelet–Fibrinogen Interaction in Thrombasthenia", Blood 55:169–178 (1980).

Coller et al., "Collagen–Platelet Interactions: Evidence for a Direct Interaction of Collagen with Platelet GPIa/IIa and an Indirect Interaction with Platelet GPIIb/IIIa Mediated by Adhesive Proteins", 74:182–192 (1989).

Coller et al., 1983. A murine monoclonal antibody that completely blocks the binding of fibrinogen to platelets produces a thrombasthenic–like state in normal platelets and binds to glycoproteins IIb and/or IIIa. J. Clin. Invest. 72: 325–338.

Furlan et al., 1987. Exposure of platelet binding sites in von Willebrand factor by adsorption onto polystyrene latex particles. Biochem. Biophys. Acta 924: 27–37.

Savage et al., Jun. 1992. Modulation of platelet function through adhesion receptors. A dual role for glycoprotein IIb–IIIa . . . J. Biolog. Chem. 267: 11300–11306.

Hynes, 1987. Integrins: a family of cell surface receptors. Cell 48: 549–554.

Pfueller et al., 1978. Role of plasma proteins in the interaction of human platelets with particles. Thrombosis Res. 12: 979–990.

Ikeda et al., 1991. The role of von Willebrand factor and fibrinogen in platelet aggregation under varying shear stress. J. Clin. Invest. 87:1234–1240.

Abrams et al., 1991. Immunological detection of activated platelets in clinical disorders. Thrombosis and Haemostasis 65: 467–473.

Rinder et al., 1991. Progressive platelet activation with storage . . . Transfusion 31: 409–414.

*Primary Examiner*—James C. Housel
*Assistant Examiner*—James L. Grun
*Attorney, Agent, or Firm*—Viviana Amzel; Pretty, Schroeder & Poplawski, PC

[57] ABSTRACT

The invention provides a method for determining platelet function in a mammal comprising providing platelets from the mammal, contacting the platelets in suspension with at least one immobilised ECM protein or an effective fragment or analog thereof while applying to the platelets an effective mechanical stimulus for an effective period of time and determining the platelet activation produced.

The invention provides a method for monitoring the efficacy of pharmacological agents affecting platelet function in vivo and in vitro.

6 Claims, 8 Drawing Sheets

METHODS FOR DETERMINING PLATELET FUNCTION

PRIOR PATENT APPLICATIONS

This is a continuation of U.S. patent application Ser. No. 07/985,679, filed Dec. 3, 1992, now U.S. Pat. No. 5,427,913.

FIELD OF INVENTION

This invention relates to methods for determining platelet function and detecting platelet dysfunction.

BACKGROUND OF THE INVENTION

Defects of platelet function are associated with abnormal bleeding conditions, including easy bruising, petechiae and purpura and are a common cause of excessive bleeding due to surgery or trauma. Hyper-responsive platelets may predispose to thrombosis, embolism, ischemia and infarction. It is therefore desirable to be able to determine platelet function and to diagnose platelet dysfunction by reliable and convenient in vitro tests, which reflect meaningfully on platelet function in vivo.

Presently available tests of platelet function include tests relating to clotting time, such as Bleeding Time, and tests involving evaluation of platelet response to activating agents such as thrombin, fibrillar collagen and ADP.

None of these tests have proved good predictors of platelet function in vivo. Probably the best available test for predicting abnormal bleeding during surgery is the Bleeding Time, but even this is poorly predictive.

An important trigger for primary platelet activation in vivo is contact with the subendothelial basement membrane exposed due to damage to the endothelial lining of blood vessels or contact with the intima of the vessel wall through more severe injury, or rupture of an atherosclerotic plaque.

Various lines of investigation suggest that cells and platelets may show a response to an immobilised activating agent which is different from the response of the same cell or platelet to that agent in soluble form. (Schwartz et al., (1991) Proc. Natl. Acad. Sci., vol. 88, pp. 7849–7853; Griffith et al., (1991), Blood, col. 78, pp. 1753–1759).

Tests of platelet activation by soluble agonists may, therefore, not reflect the relevant events involved in haemostasis or thrombosis in vivo.

Coller et al., (1989), *Blood*, vol. 74, p. 182, have examined platelet agglutination in response to immobilised collagen with a view to identifying the molecular receptor for collagen on the platelet surface. They did not, however, examine collagen-induced agglutination in relation to any clinical conditions.

Coller et al., (1980), *Blood*, vol. 55, p. 169, also examined platelet agglutination in response to immobilised fibrinogen and noted an impaired response in two patients with thrombasthenia, a condition known to be associated with an abnormality of platelet-fibrinogen interaction.

A need remains for a convenient clinical test which will reflect physiologically relevant in vivo function or dysfunction of the platelet.

SUMMARY OF INVENTION

A method is provided for determining platelet function in a mammal comprising (a) providing platelets from the mammal; (b) contacting the platelets in suspension with at least one imniobilisei extracellular matrix (ECM) protein or an effective fragment or analog thereof while applying to the platelets an effective mechanical stimulus for an effective period of time; and (c) determining the platelet activation produced.

DETAILED DESCRIPTION OF THE DRAWINGS

DETAILED DESCRIPTION OF INVENTION

Platelet activation in vivo is a complex phenomenon, involving a cascade of events. The first step is thought to involve binding or adhesion of platelets to a substrate, such as exposed subendothelial basement membrane. This is followed by activation of the platelets, leading to ATP release and aggregation of the platelets ie. adhesion of plateLets to each other, as distinct from adhesion to a substrate.

The term "platelet activation" is used in the literature both to encompass the complete cascade and to refer specifically to the later stage of the process involving platelet aggregation and ATP release.

The phrase "platelet activation" will be used herein to refer to the stage involving platelet aggregation and ATP release unless explained otherwise in a particular context.

In vitro investigations of platelet responses, particularly studies directed to adhesive interactions observed in vitro, may be difficult to relate to events in vivo under haemodynamic conditions. This difficulty is reflected in the lack of available tests of platelet function showing good correlation with physiologically relevant conditions, such as bleeding disorders.

The present inventors have found that extracellular matrix (ECM) proteins which have been immobilised, for example by attachment to microparticles, if contacted with platelets in association with a mechanical stimulus, cause platelet activation by a novel pathway, not stimulated by soluble ECM proteins, nor by the immobilised ECM proteins in the absence of the mechanical stimulus.

The method of the invention offers a novel means of assessing the integrity of a physiologically relevant platelet activation pathway.

There is thus provided a means of detecting, by a convenient clinically applicable method, dysfunctions of this platelet response pathway which manifest themselves in vivo as disordered platelet behaviour, as, for example, in thrombotic conditions or bleeding disorders.

In accordance with one embodiment of the invention, a method is provided for determining platelet function by contacting the platelets in vitro with at least one immobilised ECM protein or a fragment or analog thereof while applying to the platelets an effective mechanical stimulus, and determining the platelet activation produced.

In accordance with a further embodiment of the invention, the ECM protein or proteins are immobilised by binding to polystyrene latex beads and are brought into contact with the platelets by mechanical stirring of the solution in which the platelets are suspended.

The use of beads is convenient for several reasons: a) it enables control over the surface area, and hence quantity of the activating agent to be presented and b) it enables platelet-platelet adhesion and degranulation to be studied in suspension. Other types of particulate solid support may also be employed to immobilise the ECM proteins, for example, immunogold particles.

Suitable ECM proteins for use in the method of the invention include von Willebrand factor (vWf), fibrinogen, collagen, fibronectin, thrc)mbospondin and vitronectin.

The ECM protein employed may be bound directly to the solid support or may be bound indirectly, for example to a spacer molecule such as a synthetic peptide which is itself bound to the bead, as will be understood by those skilled in the art. Binding between spacer molecule and ECM protein may be covalent or non-covalent. Such variations are included within the scope of the invention. As seen in Example 1, the ECM protein may also be bound to an appropriate antibody which is bound to the solid support. An antibody fragment may also be used.

Effective fragments or analogs of an ECM protein may also be immobilised and used in the method of the invention and are included within the scope of the invention. For example, the effect of an immobilised ECM protein on its receptor may be mimicked by the binding of an antibody directed against that receptor, or of a fragment of such an antibody, as will be understood by those skilled in the art (Schwartz et al., (1991), Exp. Cell Res., vol. 195, p. 533). Use of such an analog of an ECM protein is included within the scope of the invention.

The mechanical stimulus applied to the platelets in conjunction with exposure to immobilised ECM proteins may be conveniently provided by stirring the platelet suspension in contact with the immobilised ECM protein.

As will be understood by those skilled in the art, other methods of applying a mechanical stimulus may be employed.

The effects of stirring speed and of bead size on the platelet activation determined by the method of the invention have been examined.

As can be seen in Example: 3, when vWf was immobilised on beads of mean diameter less than about 3.0 $\mu$m, contact with platelets did not elicit significant aggregation or ATP release. Response was maximal with beads of mean diameter about 4 $\mu$m and decreased when bead size increased beyond about 4.6 $\mu$m. Controlling for density of vWf molecules on the bead surface and for platelet/bead ratio produced identical results.

Platelet aggregation and ATP release in response to immobilised vWf were insignificant at stirring speeds below about 300 rpm and increased to a maximum value at about 500 rpm stirring speed, declining at higher stirring speeds, as seen in Example 4 and FIG. 2. These data indicate the importance of the mechanical stimulus to the platelet response determined by the method of the invention.

It was found that platelets had to be stirred in contact with immobilised vWf for at least about 3 minutes to elicit ATP release, as seen in Example 12.

In accordance with a preferred embodiment of the invention, platelet function is determined by contacting the platelets, in platelet rich plasma, with vWf immobilised on polystyrene beads of a diameter in the range of about 4 $\mu$m to about 4.6 $\mu$m with stirring at a speed in the range of about 300 rpm to about 700 rpm for a period of about 3 minutes to about 10 minutes, followed by determination of platelet activation.

In accordance with an especially preferred embodiment, bead diameter is about 4.2 $\mu$m, stirring is at about 500 rpm for about 5 minutes and platelet activation is determined as aggregation or ATP release.

Platelet response may be measured by any suitable assay method for platelet activation, including ATP release, aggregometry, measurement of second messengers such as intracellular calcium level or intracellular pH, measurement of production of activation dependent metabolites such as thromboxane B2 or arachidonic acid release or measurement of activation dependent phosphorylation of platelet proteins.

The optimum bead size, stirring speed and stirring time may vary according to the type of bead used, the particular ECM protein employed. and the size of the mixing vessel but can be readily determined by those skilled in the art.

It has been found by the inventors that platelet activation by immobilised vWf with stirring is inconsistent if washed platelets are employed. Platelets should be prepared as platelet rich plasma as described in Example 2.

Platelet activation in response to immobilised vWf as determined by the method of the invention was examined in 39 normal subjects and the range of values found was 146–923 pmol ATP released/$10^8$ platelets (Example 10).

That the observed platelet response is dependent on interaction with immobilised vWf, and is absent when soluble vWf is used as agonist, is indicated by the lack of platelet activation seen in controls employing bovine serum albumin bound to polystyrene beads (FIG. 1), since PRP from normal subjects will contain soluble vWf.

It has been found, surprisingly, that when platelet activation in response to immobilised vWf in association with a mechanical stimulus is determined by the method of the invention in platelets from patients presenting with bleeding disorders, good discrimination of these patients from normals is achieved based on the levels of platelet activation observed, as can be seen from Examples 11 and 12.

As seen in Table 5, of eighteen patients with bleeding disorders examined, only three showed ATP release within the normal range after 5 minutes of exposure of the platelets to immobilised vWf with stirring, ie. 83% detection of abnormality. Of these three, one patient showed a significantly prolonged lag time to platelet activation compared to the control.

In contrast, as seen in Table 4, conventional tests of platelet function provided poor discrimination between normal subjects and patients with bleeding disorders.

Figure 7A:
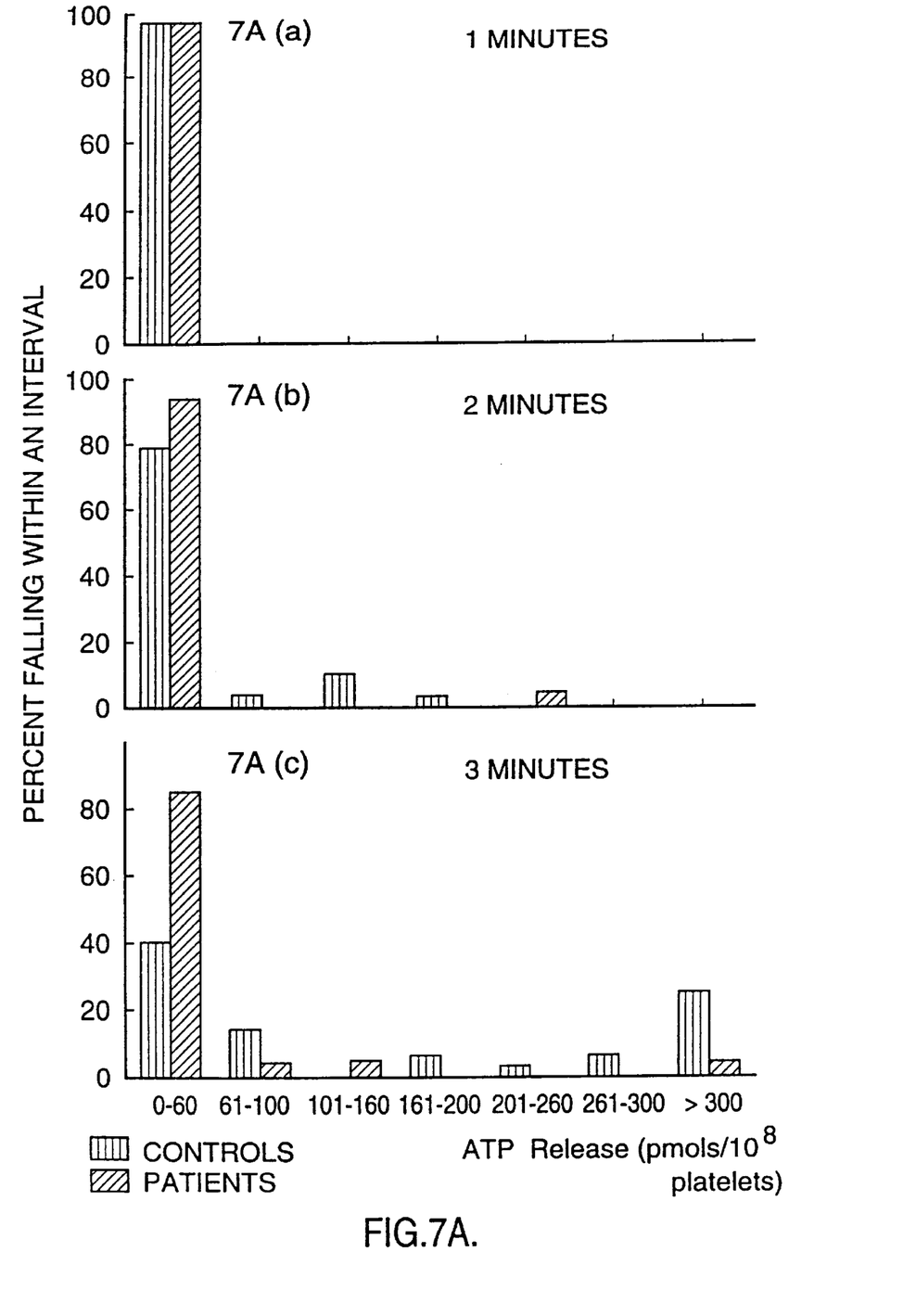
FIGS. 7A and 7B show ATP release in response to immobilised vWf after various times of exposure.
Figure 7B:
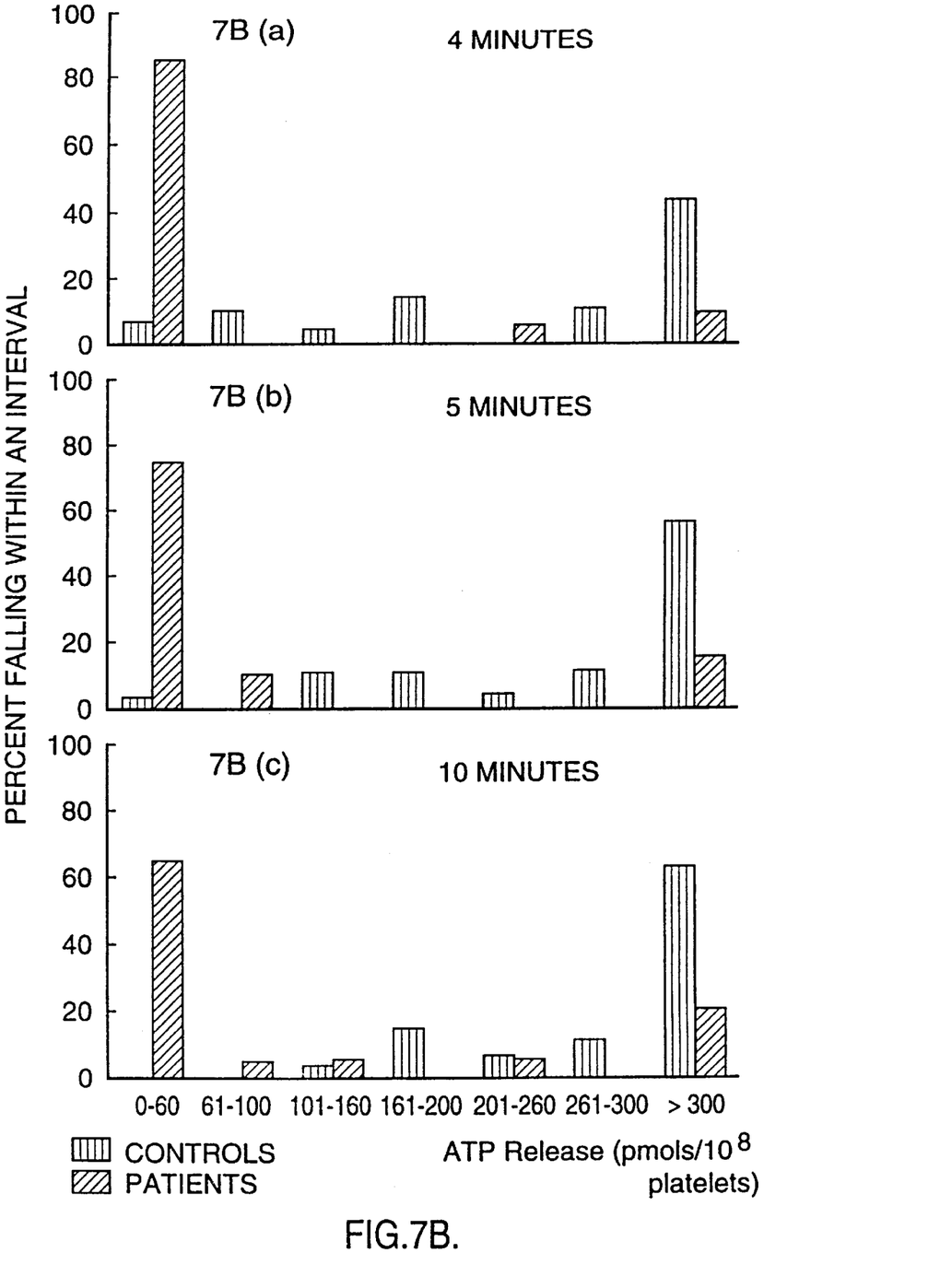

A review of ATP release in normals and patients after different time periods of platelet exposure to immobilised vWf and stirring showed that optimal discrimination between normal subjects and patients with bleeding disorders was obtained with about 5 minutes of stirring, as seen in Example 12 and FIG. 7. Below about three minutes, there was little ATP release in either normals or patients.

A further indication that the observed response is specific to bound vWf is the finding that platelet aggregation and ATP release in response to immobilised vWf in the presence of a mechanical stimulus was prevented by addition of F(ab')$_2$ fragments of a polyclonal antiserum directed against vWf.

Examination of some of the characteristics of the platelet activation observed by the inventors has demonstrated that it involves a novel response pathway, distinguishable from previously reported platelet responses.

Aggregation and ATP release in response to immobilised vWf were inhibited by monoclonal antibodies to GPIb (AN51, AP1), GPIIb-IIIa (MCA 467, P2) and GPIIIa (SZ21) but not by monoclonal antibodies to GPIV or the β1-integrin subunit (4B4).

When platelets were pre-incubated with acetyl salicylic acid (ASA) or the thromboxane analogue BM 13.177 before exposure to immobilised vWf with stirring, platelet activation was severely reduced, (Example 5) indicating that platelet activation as determined by the method of the invention is dependent on an intact thromboxane pathway. This is in contrast to the platelet agglutination observed by Coller (1980, supra) which was not inhibited by ASA.

Ingestion of ASA also leads to lowered platelet activation in response to immobilised vWf associated with a mechanical stimulus, as see in Example 13.

When platelet activation by immobilised vWf is determined by the method of the invention in order to detect bleeding disorders, subjects should not be taking aspirin or any other substance which will suppress or inhibit the thromboxane pathway.

As well as providing a novel method for determining physiologically relevant platelet activation, the method of the invention provides a means of monitoring the efficacy of agents affecting platelet function in vivo or in vitro. Such agents may be directed either to stimulating or to reducing or preventing platelet activation.

For example, drugs which depress platelet function, such as aspirin, sulfinpyrazone or dipyridimole are commonly used as anti-thrombotic agents in humans but there is presently no convenient method of monitoring their effect on platelet function induced by a physiologically relevant stimulus.

In accordance with a further embodiment of the invention, platelet activation by immobilised vWf is determined by the method of the invention before the beginning of anti-thrombotic therapy and at intervals during therapy. One can thereby determine the efficacy of a particular anti-thrombotic agent in depressing platelet function in an individual patient and select the drug most efficacious for that patient.

In accordance with a further embodiment of the invention, platelet activation is determined by contacting the platelets with collagen immobilised on polystyrene beads. Similar platelet activation was seen in response to immobilised collagen when platelets were prepared either as PRP as in Example 2 or as a washed platelet preparation as in Example 7.

Figure 4:
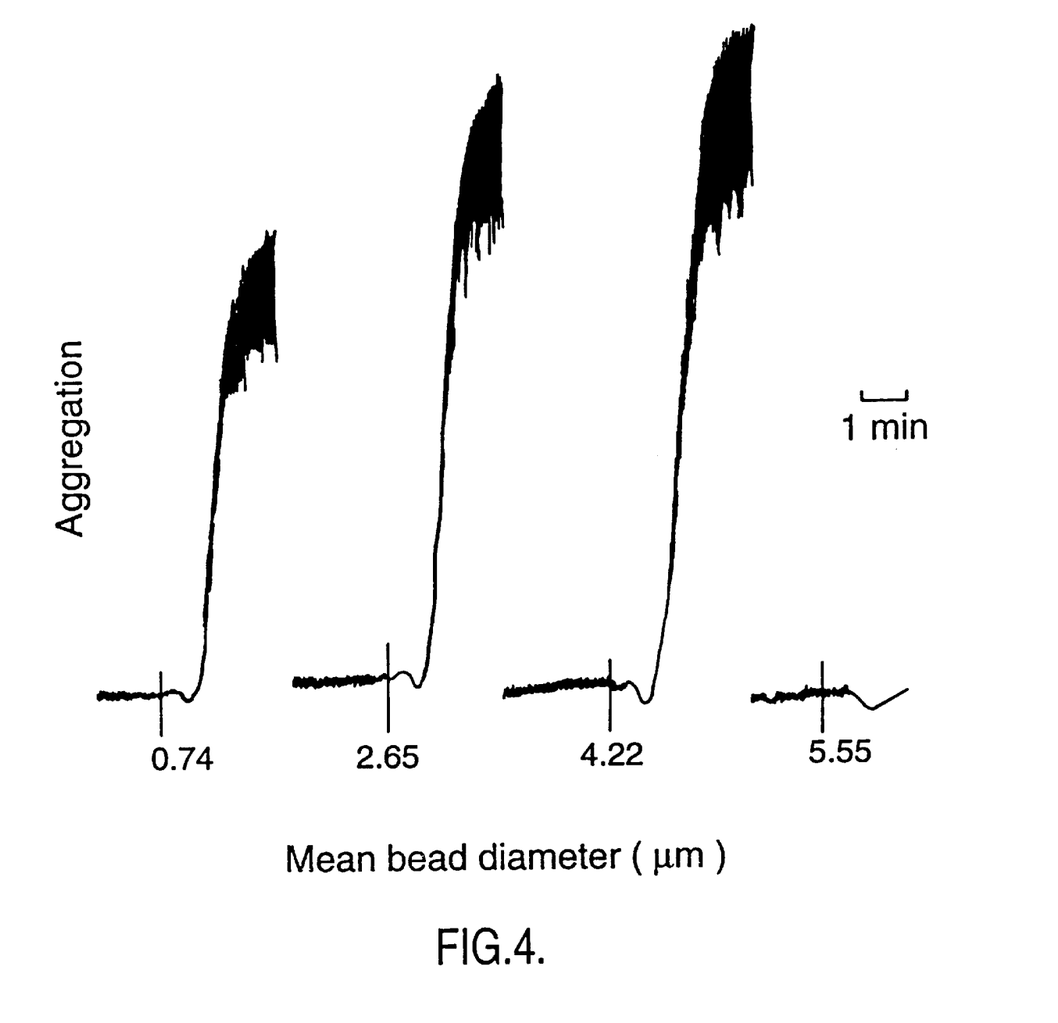
FIG. 4 shows aggregation in response to collagen immobilised on beads of various sizes.

As seen in Example 7, platelet aggregation was stimulated by collagen bound to beads of diameter 0.74 μm and platelet response increased with bead size up to a diameter of 4.22 μm. At bead sizes larger than 4.22 μm, platelet aggregation decreased sharply, as seen in FIG. 4.

Figure 5:
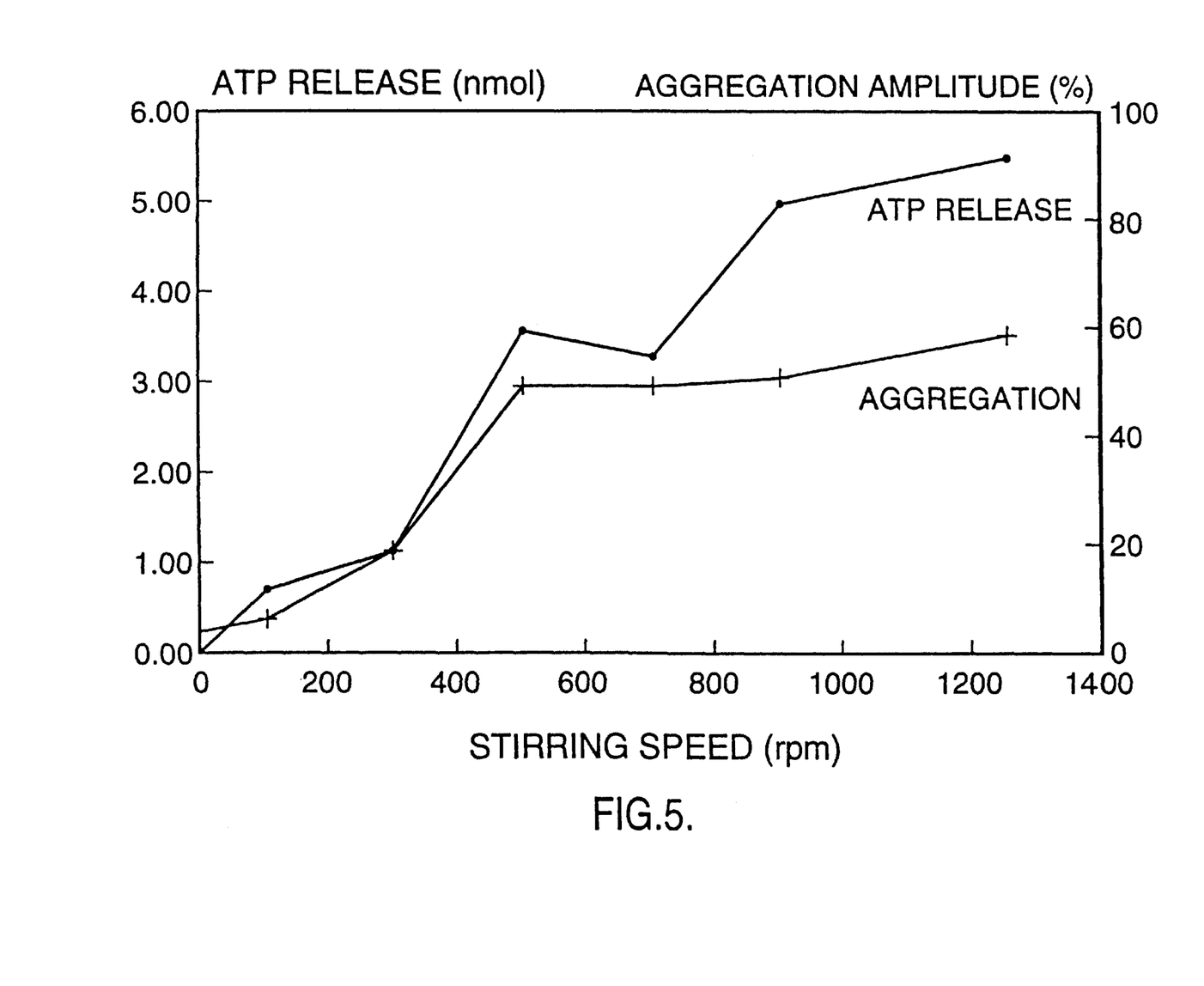
FIG. 5 shows ATP release (■) and aggregation (+) in response to immobilised collagen in relation to stirring speed.

Platelet aggregation and ATP release in response to immobilised collagen were insignificant at stirring speeds below about 200 rpm. Platelet aggregation increased with stirring speed up to about 500 rpm and remained substantially constant at higher stirring speeds, as seen in FIG. 5, whereas ATP release increased with stirring speed up to about 1200 rpm.

Platelet aggregation and ATP release in response to immobilised collagen were observable after about 30 seconds of stirring.

In accordance with a further embodiment of the invention, platelet function is determined by contacting the platelets with collagen immobilised on polystyrene beads of diameter about 4.2 μm with stirring at about 900 rpm for a period of about 2 minutes, followed by determination of platelet activation.

As with the response to immobilised vWf, platelet aggregation in response to immobilised collagen in the presence of a mechanical stimulus was inhibited by monoclonal antibodies to GPIb (AN51, AP1), GPIIb-IIIa (MCA 467, P2) and GPIIIa (SZ21) but not by monoclonal antibodies to GPIV. However the β1-integrin subunit monoclonal antibody (4B4) did inhibit immobilised collagen-induced aggregation.

Figure 6:
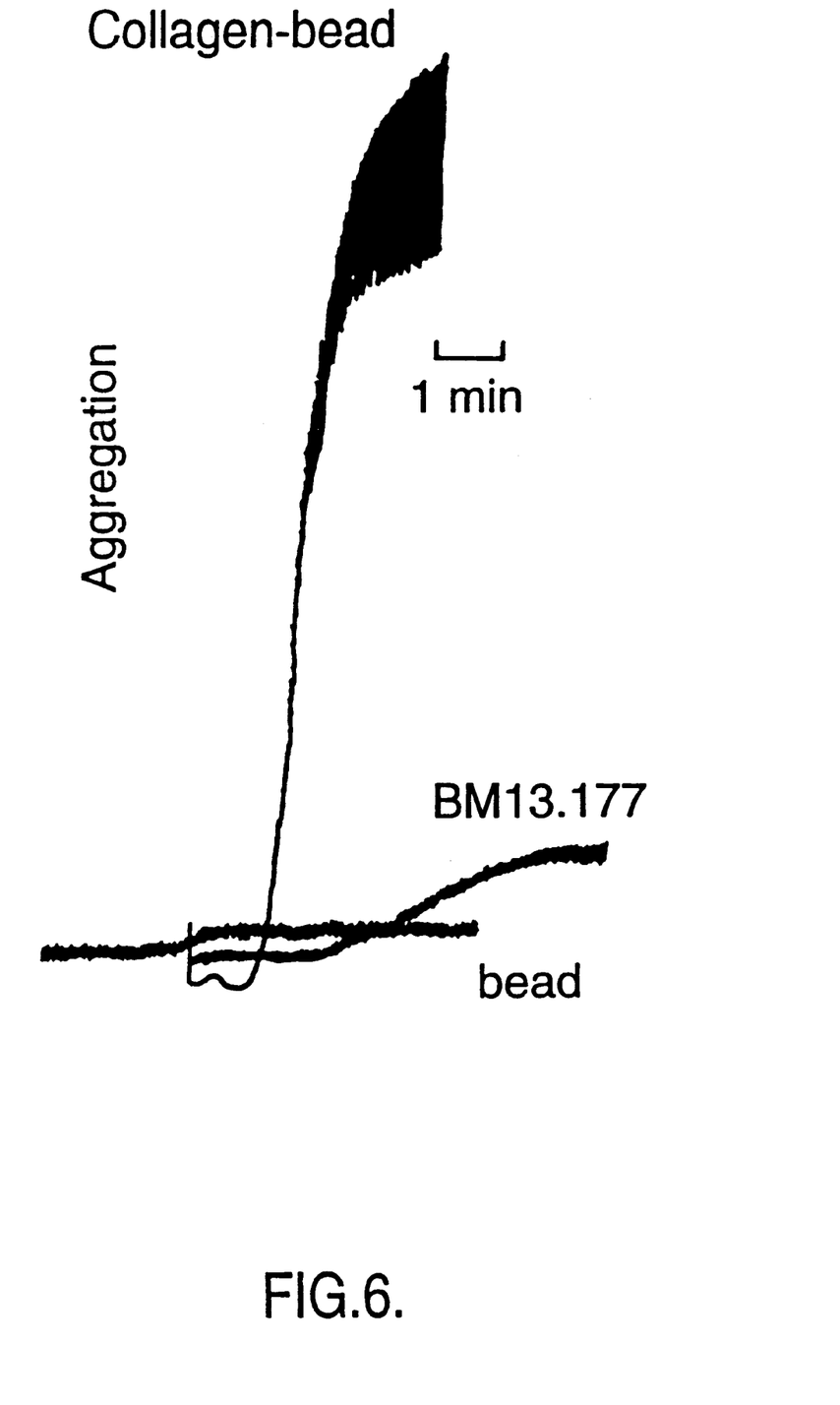
FIG. 6 shows effect of BM13.177 on platelet aggregation in response to immobilised collagen.

Platelet aggregation in response to immobilised collagen was inhibited by pre-incubation with the thromboxane inhibitor BM13.177, as seen in FIG. 6, indicating that an intact thromboxane pathway is required for the response.

When platelets were exposed to solubilised hydrolysed collagen and BSA-coated beads with stirring, no platelet activation was seen, indicating that the response is dependent on platelet interaction with immobilised collagen.

The platelet function determined by the method of the invention, whether stimulated by immobilised collagen or immobilised vWf, shows dependence on the application of a mechanical stimulus and on the presence of an intact thromboxane pathway.

The following examples are illustrative only, for the purpose of describing the process of the invention and the invention is not limited thereto.

EXAMPLE 1

Preparation of Immobilised vWf

Materials and Methods

Purified vWf:

vWf was purified from 4 mL of cryoprecipitate obtained from a pool of 16 type O donor units by the method of Thorell and Blomback (14). Purity of the preparation was assessed by crossed immunoelectrophoresis using rabbit anti-human plasma in the second dimension (Dimension Laboratories, Mississauga, Ont., Canada).

A single precipitin arc was obtained with mobility identical to that obtained using monospecific anti-vWf antibody for precipitation.

Polyclonal anti-human vWf F(ab')$_2$ fragments were purchased from American Diagnostics through Inter-Haematol (Hamilton, Ontario).

Attachment of vWf to Beads:

Polystyrene beads obtained from Polysciences Corporation through Analychem (Markham, Ont., Canada) were washed three times with distilled water prior to use.

The beads were either coated with purified vWf or were first coated with polyclonal anti-vWf F(ab')$_2$ fragments which were used to capture vWf from the purified vWf preparation.

vWf or F(ab')$_2$ fragments were adsorbed to the bead under alkaline conditions. Briefly, vWf or antibody fragments were diluted in 0.2 mol/L carbonate buffer and mixed with polystyrene beads pre-equilibrated in carbonate buffer. The mixture was incubated overnight at 4 degrees C then washed free of unbound protein with three washes in normal saline. The beads were blocked with 1% (w/v) bovine serum albumin in saline. If the beads were initially coated with antibody fragments, purified vWf was then incubated with the beads for 1 hour at 37 degrees followed by three washes in normal saline. vWf bound to the beads was quantitated using a competitive ELISA procedure (Brien et al., (1986), Clin. Bioch., vol. 19, p. 179). BSA bound to beads served as control.

Figure 1:
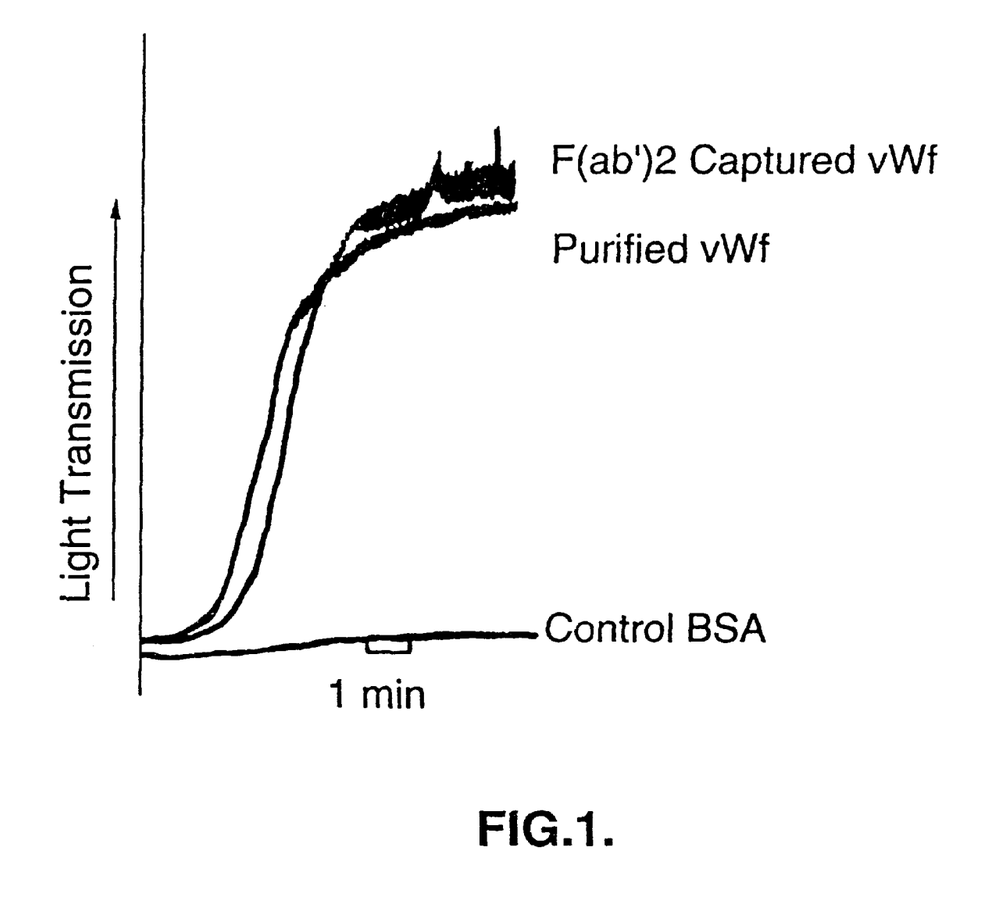
FIG. 1 shows platelet activation by immobilised purified von Willebrand factor (vWf) and immobilised F (ab')$_2$ captured vWf.

"F(ab')$_2$ captured" vWf beads produced similar platelet activation (aggregation and ATP release) to that seen with purified vWf bound directly to the beads, as seen in FIG. 1. Both preparations are included in the phrase "immobilised vWf" as used herein. "F(ab')$_2$ captured" vWf beads were used in all subsequent examples.

Other ECM proteins or fragments thereof, including fibronectin, vitronectin and thrombospondin, may also be bound to beads at alkaline pH, as will be understood by those skilled in the art.

Derivatised beads (eg. CNBr activated, carbodiimide or hydrazide activated) may also be used, which permit covalent binding of proteins to the beads.

Beads of other materials such as polyacrylonitrile may also be employed.

EXAMPLE 2

Platelet Activation by Immobilised vWf

Platelet Preparation:

Venous blood was collected from normal volunteers into one tenth volume 3.8% trisodium citrate after informed consent. Platelet rich plasma (PRP) was obtained by centrifugation of the whole blood at 150×g for 10 minutes at 22 degrees C. Preparations used had a platelet count in the range 200–400×10$^9$/L.

Platelet Activation:

Platelet activation was evaluated by determining platelet aggregation by light transmission techniques or by determining ATP release.

ATP release was determined using the firefly luciferin/luciferase system, in a Chronolog model 560VS dual channel lumi aggregometer Linked to a Chronolog 810 data reduction system purchased from Chronolog Corporation, Haverton, Pa., using reagents and procedure as outlined by the manufacturer.

Platelet aggregation was determined using the same machine, following the procedure outlined by the manufacturer.

For determining ATP release, 10 µl bead suspension (prepared as in Example 1; 1–2 units vWf/10$^8$ beads), 240 µl PRP and 15 µl chrono-lume reagent were mixed in a 6 mm internal diameter cylindrical siliconized cuvette at 37°. The mixture was stirred with a magnetic stirrer at 500 rpm for 10 minutes and ATP release was measured.

Platelet aggregation was quantitated by measuring light transmission. In each assay, normal platelets were used as control and the aggregation seen in test samples was expressed as a percentage of the light transmission seen in the normal control, which was taken as 100%.

EXAMPLE 3

Effect of Bead Size

Various sizes of polystyrene beads were obtained and coated with vWf as described in Example 1. The bead size classes were as follows: mean bead diameter 0.8 µm±0.1, 1.4 µm±0.1, 1.6 µm±0.1, 2.9 µm±0.1, 4.2 µm±0.1, 4.6 µm±0.1 and 5.8 µm±0.1.

Platelet activation in response to stimulation by these vWf-coated beads was determined as described in Example 2 and the results are shown in Table 1.

Further examples of response to immobilised vWf used 4.2 µm beads unless otherwise stated.

TABLE 1

| Bead Diameter (µm) | Aggregation % | ATP Release (pmol) |
|---|---|---|
| 0.8 | 0 | 0 |
| 1.4 | 5 | 0 |
| 1.6 | 11 | 0 |
| 2.9 | 11 | 0 |
| 4.2 | 70 | 320 |
| 4.6 | 50 | 280 |
| 5.8 | 41 | 220 |

EXAMPLE 4

The effect of stirring speed on platelet activation in response to immobilised vWf was examined.

Platelet activation was determined by aggregation and ATP release in accordance with the procedure described in Example 2.

Figure 2:
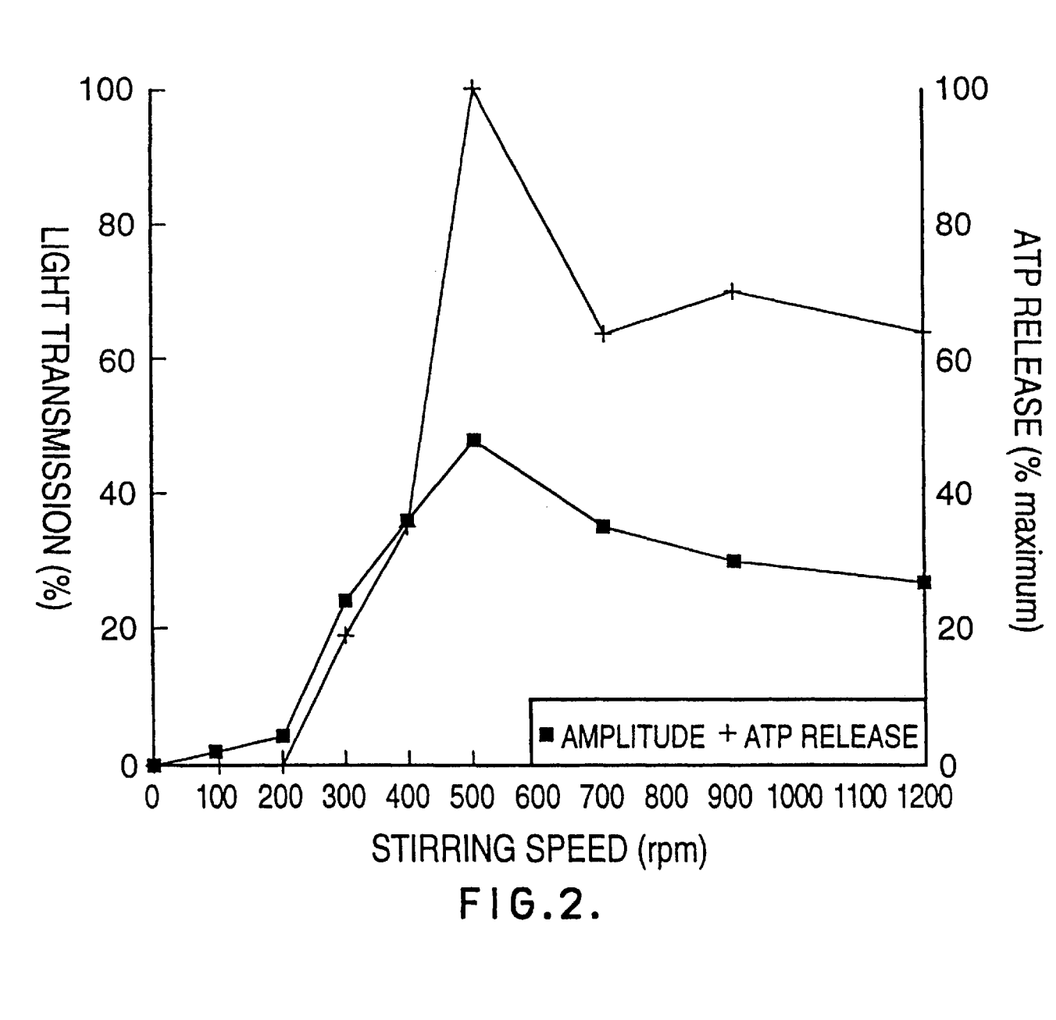
FIG. 2 shows ATP release (■) and aggregation (+) in response to immobilised vWf in relation to stirring speed.

The results are shown in FIG. 2. Both aggregation and ATP release increased with stirring speed up to a maximum value at a stirring speed around 500 rpm. At speeds greater than 500 rpm, both aggregation and ATP release declined.

EXAMPLE 5

The in vitro effects of acetyl salicylic acid (ASA) and the thromboxane analogue BM13.177 (gift of Dr. Stegmeier, Boehringer-Mannheim, Germany) on platelet aggregation in response to immobilised vWf in conjunction with a mechanical stimulus were examined. Both of these substances inhibit the thromboxzone pathway.

Venous blood was obtained from normal subjects and PRP prepared as in Example 2.

Figure 3:
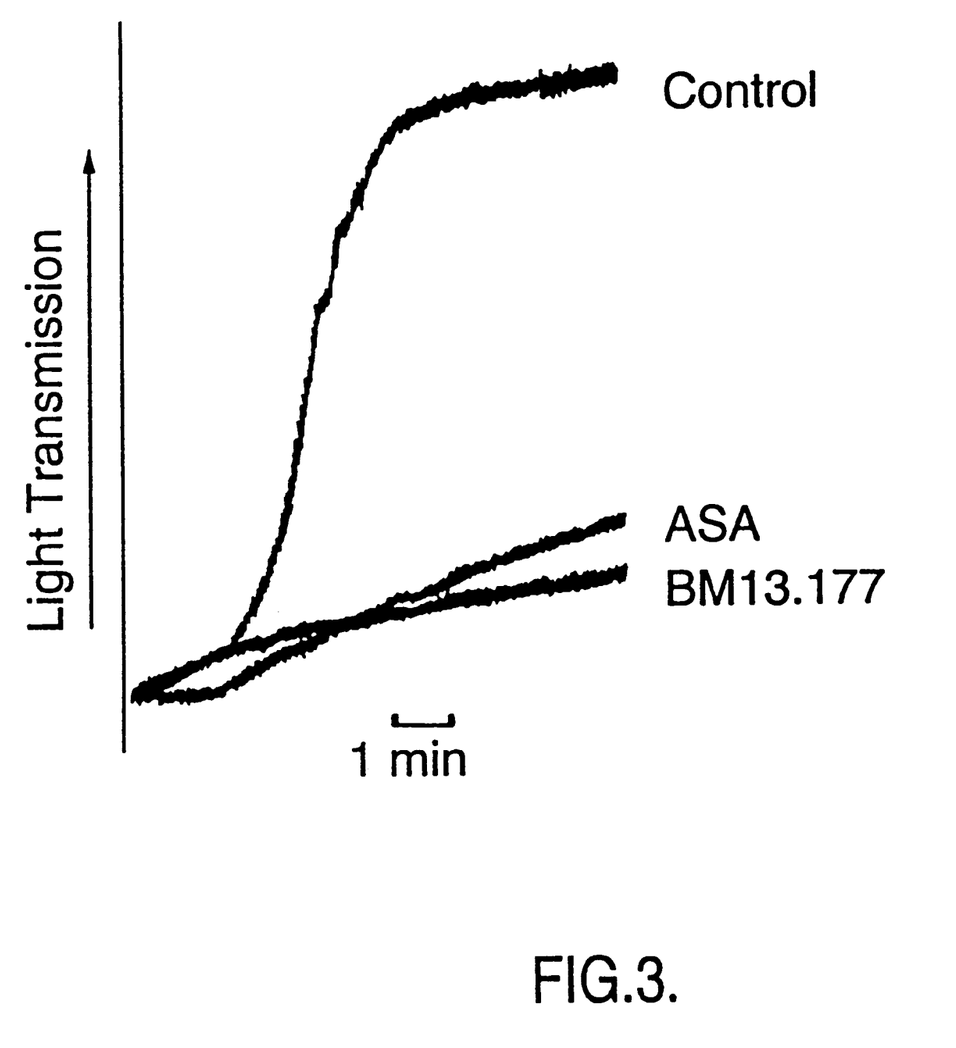
FIG. 3 shows effect of acetyl salicylic acid (ASA) and BM13.177 on platelet aggregation.

Aggregation was determined as described in Example 2, with addition of 500 µM ASA or 450 µM BM13.177, which were pre-incubated with the platelets for 15 and 10 minutes respectively before addition of immobilised vWf. The results are shown in FIG. 3.

The effects of ASA and BM13.177 on ATP release were also examined.

The results are shown in Tables 2 and 3.

TABLE 2

| Subject TI - | Without BM13.177 | 190 pmol ATP release |
|---|---|---|
| | With BM13.177 | 30 pmol ATP release |
| Subject MS - | Without BM13.177 | 540 pmol ATP release |
| | With BM13.177 | 32 pmol ATP release |
| Subject LM - | Without BM13.177 | 335 pmol ATP release |
| | With BM13.177 | 0 pmol ATP release |
| Subject MS - | Without BM13.177 | 372 pmol ATP release |
| | With BM13.177 | 25 pmol ATP release |
| Subject BB - | Without BM13.177 | 545 pmol ATP release |
| | With BM13.177 | 32 pmol ATP release |

TABLE 3

| Subject LM - | Without ASA | 370 pmol ATP release |
|---|---|---|
| | With ASA | 13 pmol ATP release |
| Subject MS - | Without ASA | 279 pmol ATP release |
| | With ASA | 6 pmol ATP release |

EXAMPLE 6

Preparation of Immobilised Collagen

Purified pepsin-solubilised bovine dermal collagen (Collagen Corporation, Palo Alto, Calif.) in 0.012N HCl (pH 2.0) was adjusted to pH 3.5 and incubated with polystyrene beads at 4° C. for 16–18 hours at a concentration of 3.0 mg/ml collagen.

The protein was non-covalently bound to the beads. The beads were washed several times in buffer to remove excess protein and the remaining binding sites blocked by coating with bovine serum albumin. Beads were stored in Hepes buffer pH 7.1. The shelf life in carbonate buffer is at least seven days.

As described for vWf, collagen may also be bound indirectly to the beads via an antibody or antibody fragment or via a spacer molecule.

EXAMPLE 7

Platelet activation in response to immobilised collagen prepared as in Example 6 was determined by a procedure similar to that described in Example 2.

Collagen was immobilised on beads of various size and the effect of bead size on platelet response was examined. Bead sizes were as follows:

mean bead diameter 0.74 $\mu$m±0.1, 2.65 $\mu$m±0.1, 4.22 $\mu$m±0.1 and 5.55 $\mu$m±0.1.

Washed platelets were prepared from normal venous blood after addition of apyrase and prostacyclin as described by Griffith et al., (1991), *Blood*, vol. 78, p. 1753.

Platelets were stirred with immobilised collagen at 900 rpm for 5 minutes and aggregation and ATP release were determined as in Example 2. The results are shown in FIG. 4.

Platelet aggregation was stimulated by collagen bound to beads of diameter 0.74 $\mu$m and increased with bead size up to a diameter of 4.22 $\mu$m. At larger bead sizes, platelet aggregation decreased sharply.

EXAMPLE 8

The effect of stirring speed on platelet aggregation and ATP release in response to immobilised collagen was examined.

Collagen was immobilised on beads of diameter 2.65 $\mu$as described in Example 6, and platelet response was determined as described in Example 7. The results are shown in FIG. 5.

EXAMPLE 9

The effect of the thromboxane inhibitor BM13.177 on platelet activation by immobilised collagen was examined.

Platelets were pre-incubated with 450 $\mu$M BM13.177, before addition of immobilised collagen (2.65 $\mu$m beads). Platelet aggregation was determined as in Example 7 and the results are shown in FIG. 6.

EXAMPLE 10

Venous blood was obtained from 39 healthy adult volunteers and platelet rich plasma (PRP) was prepared as described in Example 2.

Platelet activation (ATP release) in response to immobilised vWf was determined by the procedure of Example 2, using 4.2 $\mu$m beads and stirring at 500 rpm for 5 minutes.

The range of values found in these normal subjects was 146–923 pmol ATP/$10^8$ platelets (Mean±1SD=433±186 pmol ATP/$10^8$ platelets). Mean aggregation value was 61.97±13.46 (S.D.)

EXAMPLE 11

Eighteen patients referred because of bleeding disorders of undetermined etiology were subjected to a battery of tests of platelet function. Most of these patients displayed "easy bruising".

The following conventional tests to assess bleeding disorders were used:

1. Bleeding Time (B.T.): normal range 0–8 minutes
2. Platelet Aggregation in response to Soluble Agonists (Platelet Aggregation):

Soluble agonists known to induce platelet aggregation in normal individuals were added to platelet rich plasma (PRP) under stirring conditions. Abnormal aggregation patterns (ie. the rate and degree of platelet clumping) are indicative of platelet dysfunction. Agonists used were adrenalin (1 $\mu$M, 5 $\mu$M, 50 $\mu$M), ADP (1 $\mu$M, 2 $\mu$M, 4 $\mu$M, 10 $\mu$M), collagen (1 $\mu$g/mL, 5 $\mu$g/mL), arachidonic acid (500 $\mu$M) and ristocetin (0.5 mg/mL, 1.2 $\mu$g/mL, 1.5 $\mu$g/mL). Methods were as described by Howard et al. (1971), Thromb. Diath. Hemrrh., vol. 26, p. 362; Born (1962), J. Physiol., vol. 162, p. 67 and Weiss (1973), J. Clin, Invest., vol. 52, p. 2697.

3. vWf concentration (vWf): vWf concentration was determined immunologically by the method of Brien et al. (1986), Clin. Biochem., vol. 19, p. 179.

Results were expressed as units per ml plasma, the arbitrary unit being defined as the activity found in 1 ml normal plasma. Normal Range 0.5–1.5 U/ml.

4. vWf biological function (RCof): assessment of vWf biological function was done using a ristocetin cofactor (RCoF) assay of MacFarlane et al., (1975), Thromb. Daith. Hem., vol. 34, p. 306.

Units and normal range as for vWf.

5. Factor VIII Complex (FVIII):

The factor VIII complex consists of a small procoagulant molecule (FVIII:C) bound to a large molecule (von Willebrand factor) (vWf). FVIII:C was quantitated based on a clotting assay indicative of its biological function rather than the absolute amount of protein in the blood. (In "Human blood coagulation, hemostasis and thrombosis", Biggs, R (Ed), (1972))

Units and normal range as for vWf.

6. Platelet Count: Normal Range 140–340×$10^9$/L
7. Prothrombin Time (PT): clotting time was determined and expressed as an International Normalised Ratio (INR). Normal Range 0.8–1.2 INR
8. Activated Partial Thromboplastin Time (aPTT): was determined as described in Cartwright, Diagnostic Lab. Hematology, 3rd. edition, p. 159 and Proctor et al., (1961), Amer. J. Clin. Path., vol. 36, p. 212.

Normal range 25.0–36.0 secs.

9. Platelet activation (ATP release) in response to immobilised vWf: determined on platelet rich plasma as described in Example 10.

The results of tests 1 to 8 are shown in Table 4. ATP release in response to immobilised vWf is shown in Table 5. Mean aggregation value was 38.24±17.58 (S.D.)

TABLE 4

| | | | | | | | | |
|---|---|---|---|---|---|---|---|---|
| JA | 7.0 | Normal response to all agonists | 0.97 | 2.50 | 1.43 | $246 \times 10^9$/L | 0.9 | 25.2 |
| AP | 10.5 | Abnormal response to arachidonic acid and ADP | 1.95 | 2.50 | 2.57 | $218 \times 10^9$/L | 1.0 | 27.6 |
| ND | 5.0 | Abnormal response to ADP | 1.07 | 1.27 | 1.23 | $268 \times 10^9$/L | 0.8 | 28.1 |
| TL | 6.0 | Normal response to all agonists | 2.20 | 4.25 | 2.24 | $221 \times 10^9$/L | 0.9 | 29.1 |
| TW | 5.5 | Normal response to all agonists | 1.33 | 1.80 | 1.68 | $245 \times 10^9$/L | 0.9 | 28.1 |
| KF | 7.0 | Abnormal response to ADP | 0.98 | 1.07 | 0.84 | $273 \times 10^9$/L | 1.0 | 37.9 |
| DB | 6.5 | Normal response to all agonists | 0.76 | 0.85 | 1.18 | $335 \times 10^9$/L | 0.9 | 30.0 |
| BP | 6.0 | Normal response to all agonists | 0.48 | 0.54 | 0.69 | $264 \times 10^9$/L | 0.9 | 30.6 |
| WC | 5.0 | Abnormal response to arachidonic acid, collagen, ADP and adrenalin | 1.28 | 1.85 | 1.70 | $432 \times 10^9$/L | 1.0 | 32.2 |
| DC | 6.5 | Abnormal response to collagen, adrenalin and ADP | 1.12 | 1.34 | 1.25 | $266 \times 10^9$/L | 0.9 | 32.5 |
| GB | 8.5 | Reduced response to adrenalin | 1.59 | 1.84 | 2.62 | $286 \times 10^9$/L | 0.9 | 27.1 |
| HA | 9.0 | Normal response to all agonists | 0.88 | 1.35 | 0.90 | $93 \times 10^9$/L | 0.9 | 30.6 |
| KE | 4.0 | Abnormal response to arachidonic acid, collagen, ADP and adrenalin | 1.48 | 1.56 | 1.65 | $262 \times 10^9$/L | 0.9 | 27.5 |
| DB | 9.0 | Slightly reduced response to low dose ADP | 0.69 | 0.94 | 1.11 | $193 \times 10^9$/L | 1.0 | 28.5 |
| EA | 5.0 | Normal response to all agonists | 1.82 | 1.35 | 2.25 | $264 \times 10^9$/L | 0.9 | 28.7 |
| KE | >20.0 | Normal response to all agonists | 1.48 | 1.56 | 1.65 | $262 \times 10^9$/L | 0.9 | 27.5 |
| FW | — | Abnormal response to collagen, adrenalin and ADP | — | — | — | $1064 \times 10^9$/L | — | — |
| TM* | 8.5 | Normal response to all agonists | 1.44 | 1.12 | 1.44 | $238 \times 10^9$/L | 1.0 | 31.5 |

*Normal subject included as blind control

TABLE 5

| | |
|---|---|
| J. A. | 13.0 pmol ATP/$10^8$ platelets |
| A. P. | 0.0 pmol ATP/$10^8$ platelets |
| N. D. | 13.0 pmol ATP/$10^8$ platelets |
| T. L. | 719.0 pmol ATP/$10^8$ platelets |
| T. W.* | 43.0 pmol ATP/$10^8$ platelets |
| K. F. | 9.2 pmol ATP/$10^8$ platelets |
| A. P. | 17.8 pmol ATP/$10^8$ platelets |
| D. B.* | 127.0 pmol ATP/$10^8$ platelets |
| B. P. | 11.6 pmol ATP/$10^8$ platelets |
| W. C.* | 75.0 pmol ATP/$10^8$ platelets |
| D. C. | 0.0 pmol ATP/$10^8$ platelets |
| G. B.* | 206.0 pmol ATP/$10^8$ platelets |
| H. A. | 385.0 pmol ATP/$10^8$ platelets |
| K. E. | 0.0 pmol ATP/$10^8$ platelets |
| D. B. | 41.0 pmol ATP/$10^8$ platelets |
| E. A. | 0.0 pmol ATP/$10^8$ platelets |
| K. E. | 0.0 pmol ATP/$10^8$ platelets |
| F. W. | 0.0 pmol ATP/$10^8$ platelets |
| T. M.** | 333.0 pmol ATP/$10^8$ platelets |

*Lag time to platelet activation significantly prolonged compared to control.
**Normal subject included as a blind control.

EXAMPLE 12

The 39 normal platelet preparations of Example 10 and the eighteen patient platelet preparations of Example 11 were used to examine platelet activation (ATP release) in response to stirring with immobilised vWf for various periods of time by the procedure of Example 10. The results are shown in FIG. 7.

EXAMPLE 13

Venous blood was obtained from three normal volunteers both before and at several time intervals after aspirin (ASA) ingestion.

PRP was prepared and ATP release in response to immobilised vWf was determined as described in Example 10 except that stirring was for 10 minutes.

The results are shown in Table 6.

TABLE 6

| | | |
|---|---|---|
| Subject LP - | Prior to aspirin ingestion | 217 pmol ATP release |
| | 2 days post aspirin ingestion | 47 pmol ATP release |
| | 10 days post aspirin ingestion | 385 pmol ATP release |

*325 mg ASA ingested

TABLE 6-continued

| | | |
|---|---|---|
| Subject MS - | Prior to aspirin ingestion | 303 pmol ATP release |
| | 12 hours post aspirin ingestion | 6 pmol ATP release |
| | 3 days post aspirin ingestion | 30 pmol ATP release |
| | 14 days post aspirin ingestion | 340 pmol ATP release |
| *325 mg ASA ingested | | |
| Subject LM - | Prior to aspirin ingestion | 340 pmol ATP release |
| | 12 hours post aspirin ingestion | 3 pmol ATP release |
| | 8 days post aspirin ingestion | 440 pmol ATP release |
| *325 mg ASA ingested | | |

The present invention is not limited to the features of the embodiments described herein, but includes all variations and modifications within the scope of the claims.

We claim:

1. A method of determining whether an agent alters platelet function, comprising
    obtaining a sample comprising suspended platelets;
    dividing the sample into a test sample and a control sample;
    contacting the test sample with the agent for a selected period of time;
    determining platelet activation for the control and contacted test samples by
        contacting the control and contacted test samples individually with an agonist comprising von Willebrand factor (vWF) immobilized on a particulate solid support to form control and test suspensions;
        applying to each of the control and test suspensions an activation stimulus consisting of a mechanical stimulus acting together with the immobilized vWF of the agonist for a period of time known to be effective for producing activation of platelets;
        determining platelet activation values for the test and control suspensions; and
        comparing the platelet activation values of the test suspension and the control suspension, wherein an activation value for the contacted test suspension lower or higher than for the control suspension indicates that the agent alters platelet function.

2. The method of claim 1, wherein the platelet activation values are determined by measuring aggregation of the test and control suspensions, measuring adenosine triphosphate (ATP) release or thromboxane B2 or arachidonic acid production of the activated platelets, or measuring intracellular calcium level or intracellular pH of the activated platelets.

3. The method of claim 1, wherein the sample comprises platelet rich human plasma.

4. The method of claim 3, wherein the vWf immobilized on a particulate solid support comprises vWf bound directly or indirectly to polystyrene beads of a diameter in the range of about 4 to 4.6 µm, the mechanical stimulus is applied by stirring the test and control suspensions; and the platelet activation values are determined by measuring aggregation of the test and control suspensions or measuring adenosine triphosphate (ATP) release from the activated platelets.

5. The method of claim 4, wherein the stirring is conducted at a speed of about 300 to 700 rpm for a period of about 3 to 10 minutes.

6. The method of claim 5, wherein the stirring is conducted at a speed of about 500 rpm for about 5 minutes, and the bead diameter is about 4.2 microns.

* * * * *